United States Patent [19]

Kok, deceased et al.

[11] Patent Number: 5,188,623

[45] Date of Patent: Feb. 23, 1993

[54] STOMAL STOP WITH BAG

[76] Inventors: Cornelis J. M. Kok, deceased, late of Amsterdam; by Sietze L. Kornelis, executrix, Rhijnvis Feithstraat 44/hs 1054 VA, Amsterdam, both of Netherlands

[21] Appl. No.: 827,459

[22] Filed: Jan. 29, 1992

Related U.S. Application Data

[63] Continuation of Ser. No. 710,364, Jun. 3, 1991, abandoned, which is a continuation of Ser. No. 272,574, Nov. 17, 1988, abandoned.

[30] Foreign Application Priority Data

Nov. 23, 1987 [NL] Netherlands .................. 87.02802
Mar. 9, 1988 [NL] Netherlands .................. 88.00585

[51] Int. Cl.$^5$ .............................................. A61F 5/44
[52] U.S. Cl. ................................ 604/328; 604/337
[58] Field of Search ............... 604/327, 328, 276, 277, 604/332, 337–339, 341, 342, 355, 358, 385.1; 600/32

[56] References Cited

U.S. PATENT DOCUMENTS

| | | | |
|---|---|---|---|
| 1,240,125 | 9/1917 | Doud | 604/328 |
| 2,452,813 | 11/1945 | Wade | 604/328 |
| 2,544,201 | 3/1951 | Wade | 604/328 |
| 2,915,065 | 12/1959 | Lyons et al. | 604/329 |
| 3,548,828 | 12/1970 | Vasile | 604/328 |
| 3,938,521 | 2/1976 | Ritota et al. | 604/328 |
| 4,067,335 | 1/1978 | Silvanov | 604/328 |
| 4,121,589 | 10/1978 | McDonnell | 604/337 |
| 4,137,918 | 1/1979 | Bogert | 604/328 |
| 4,182,332 | 1/1980 | Delaney | 604/328 |
| 4,209,009 | 6/1980 | Hennig | 600/30 |
| 4,210,131 | 7/1980 | Perlin | 600/32 |
| 4,344,434 | 8/1982 | Robertson | 600/32 |
| 4,445,899 | 5/1984 | Bond | 604/385 |
| 4,496,356 | 1/1985 | Lognion | 604/328 |
| 4,596,554 | 6/1986 | Dastgeer | 604/327 |

FOREIGN PATENT DOCUMENTS

| | | | |
|---|---|---|---|
| 0037785 | 10/1981 | European Pat. Off. | 604/335 |
| 2447996 | 4/1976 | Fed. Rep. of Germany . | |
| 7601384 | 2/1976 | Netherlands . | |
| 1109156 | 8/1984 | U.S.S.R. | 604/317 |
| 2014857 | 9/1979 | United Kingdom | 604/327 |
| 2090741 | 7/1982 | United Kingdom | 604/327 |
| 0003192 | 6/1987 | World Int. Prop. O. | 604/337 |

*Primary Examiner*—John D. Yasko
*Assistant Examiner*—Anthony Gutowski
*Attorney, Agent, or Firm*—Stetina and Brunda

[57] ABSTRACT

A stomal stop has a support which is substantially circular in cross section, one end of which is configured to be received within a stoma. The oppositely situated ends of the support are open such that material may pass therethrough. A bag is at least partially surrounded by the support such that material entering the stomal channel from said stoma is substantially deposited within the bag. A material which expands through the action of heat, fluid, or pressure is formed at least partly around the support for attaching the support to the stoma. A fluid-absorbing spongy material substantially surrounds at least a portion of the support and expands upon absorption of fluid to seal the stoma. A helical spring may optionally be disposed within the support body and tensioned by an insertion sleeve to permit passage of the support body into the stoma. Upon removal of the insertion sleeve the helical spring resiliently expands to frictionally hold the stomal channel within the stoma.

14 Claims, 2 Drawing Sheets

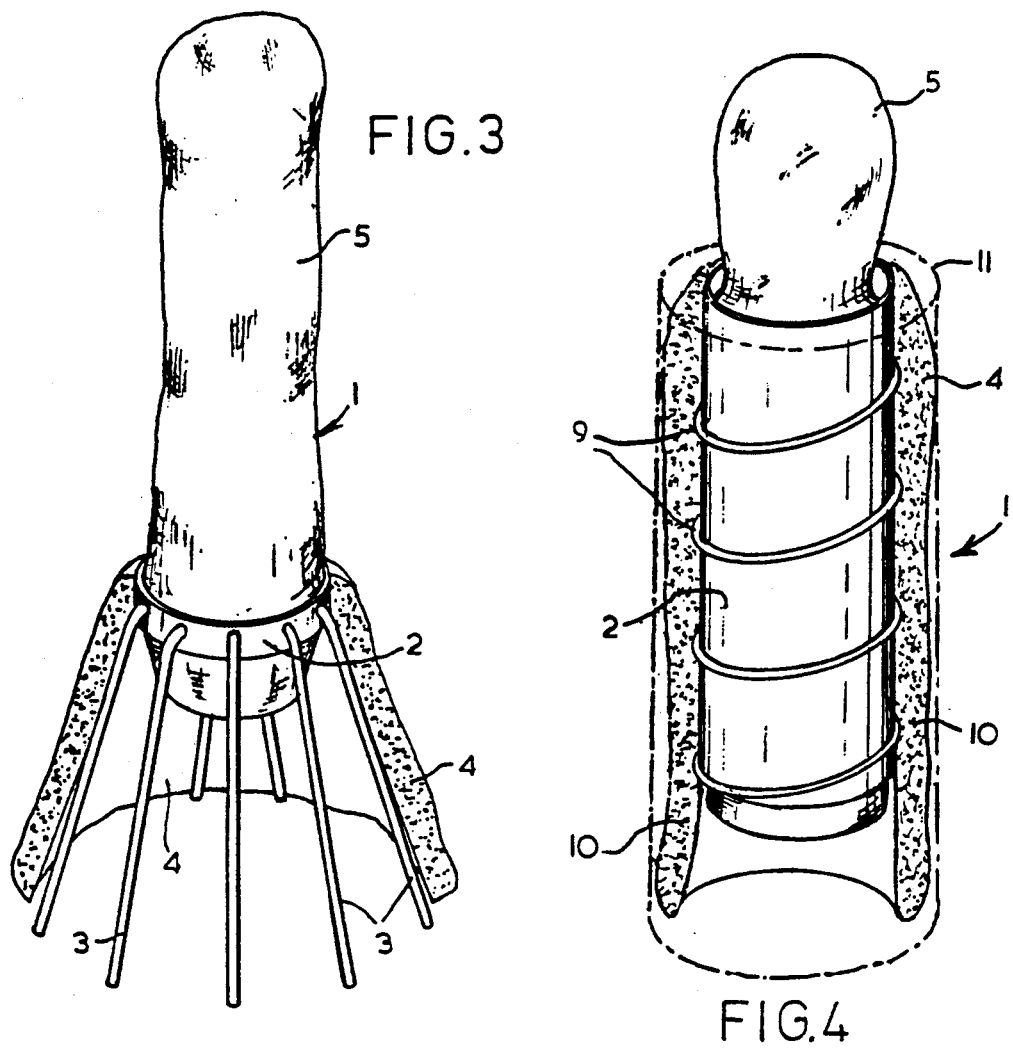
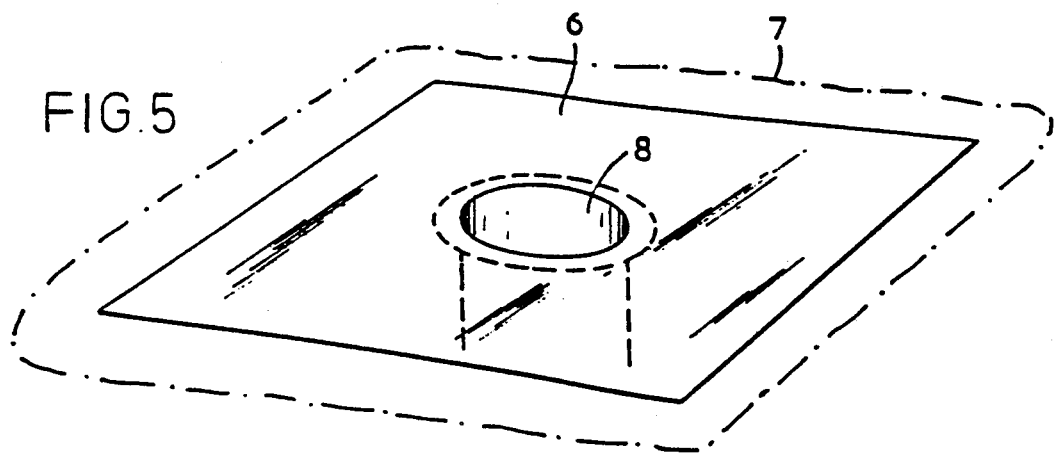

STOMAL STOP WITH BAG

This application is a continuation of Ser. No. 07/710,364 filed Jun. 3, 1991 (abandoned) which is a continuation of Ser. No. 07/272,574 filed Nov. 17, 1988 (abandoned).

FIELD OF THE INVENTION

The invention relates to a stomal stop provided with a support that is substantially circular in cross-section and whose oppositely situated ends are open, which support carries a bag open at one end.

BACKGROUND OF THE INVENTION

Such a stomal stop is known from U.S. Pat. No. 4,067,335. This known stomal stop comprises an annular support which is inserted into, for example, the anal canal of a patient. A folded or rolled-up bag closed at one end communicates with the support for the reception of faeces and/or urine. The excrements' passage into the bag causes the latter to be unrolled or unfolded. The part of the bag which contains the faeces and/or urine can be sealed and released, so that the remaining part of the bag still attached to the support is available for the reception of further waste matter from the patient's body.

One drawback of the known stomal stop is that it is of a rather complicated design and therefore expensive. This is a grave disadvantage, considering that a user of stomal stops requires at least on stomal stop a day. A further drawback of the known stomal stop is that it does not afford a proper sealing of the patient's anus. In addition, it has been found in actual practice that the bag of the known stomal stop is liable to be detached from its holding ring. And finally, the lack of compactness renders the known stomal stop rather unwieldy in use.

SUMMARY OF THE INVENTION

It is an object of the present invention to provide a simple, compact stomal stop which achieves a proper sealing of, for example the user's anus and in which the bag cannot get detached unintentionally from the support. To this end, a stomal stop of the type mentioned in the introductory paragraph is according to the invention characterized in that the support comprises means of attachment for securing the stomal stop in position in a skin cavity fo the stomal stop user and that the support surrounds the bag at least in part. Because of this design, the bag is not liable to be unintentionally detached or torn or otherwise disabled.

One embodiment of a stomal stop according to the invention is characterized in that the means of attachment contain resilient reeds disposed at one end of the support, at which end the opening of the bag is also located, whilst the bag is connected to the resilient reeds at virtually the same points where these reeds are fitted to the support. This arrangement ensures a firm positioning of the stomal stop in, for example, a patient's natural or artificial anus, because when the bag is filled with, for example faeces, it will, by its very weight, force the reeds to bend outwards. This outwardly diverging position of the reeds affords excellent gripping of the stomal stop in, for example, an artificial—whether or not temporary—opening.

A further embodiment of a stomal stop according to the invention is characterized in that the means of attachment comprise a fluid-absorbing material which has been disposed at least partly round the support and which may expand through absorption.

Yet another embodiment of a stomal stop according to the invention is characterized in that the means of attachment contain a material which may expand through the action of heat, fluid and/or pressure and which material has been disposed at least partly round the support and/or is at least partly identical with the material from which the support has been made.

A further embodiment of a stomal stop according to the invention is characterized in that before use of the stomal stop the support is at least partly enveloped in a sleeve and that the means of attachment contain a material which may expand upon removal of the sleeve, which material has been disposed at least partly round the support and/or is at least partly identical with the material from which the support has been made, whilst the said sleeve envelops the expandable material before the stomal stop is put into use. The expandable material may, for instance, be made of a polymeric substance.

A further embodiment of a stomal stop according to the invention is characterized in that the means of attachment comprise a helical spring disposed in the wall of the support, or alternatively either on the inner or on the outer wall of the support, which helical spring is tensioned before and slack after the insertion of the stomal stop into a body cavity of a stomal stop user, whilst the diameter of the helical spring is smaller when tensioned than when slack. If such a helical spring is designed so as to be hollow, gas can be passed through the cavity within the spring.

A further embodiment of a stomal stop according to the invention is characterized in that the support is surrounded at least partly by spongelike material having closed or open cells. If the spongy material contains open cells, gas can be passed through. However, spongy material containing closed cells can readily absorb fluid.

Yet another embodiment of a stomal stop according to the invention is characterized in that the support has a conical shape and that the opening of the bag is provided with a locking ring having a larger diameter than the diameter of that end of the support which faces away from the skin cavity of a patient during use of the stomal stop, whereby during use of the stomal stop the locking ring prevents the bag from leaving the support through the said end.

BRIEF DESCRIPTION OF DRAWINGS

The invention will now be elucidated with reference to the accompanying drawings, in which FIGS. 1, 2, 3 and 4 represent embodiments of the stomal stop according to the invention; and FIG. 5 depicts a strip of adhesive material with the aid of which the stomal stops of FIGS. 1, 2 and 3 can be stuck onto the skin of a patient with a stomal.

DETAILED DESCRIPTION OF THE INVENTION

Figure 1:
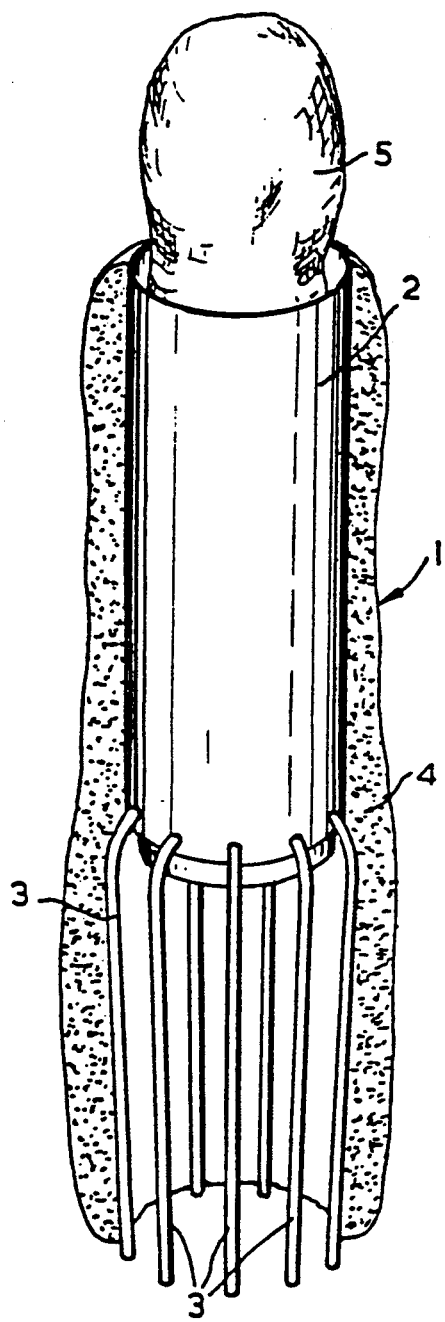

FIG. 1 shows stomal stop 1 which is formed by a cylindrical support 2. At one of its ends this support 2 carries a number of resilient reeds 3. The support 2 may have been made, for example, from a flexible material. To enhance the flexibility still further, if required, the casing of the support 2 may be provided with longitudinal indentations (not shown). The support 2 is enveloped in a fluid-absorbing material 4, for example cottonwool. A bag 5 serving for the reception of faeces and/or urine is accommodated within the support 2. To permit insertion of the stomal stop 1 into the anus of a stomal stop user, the reeds 3 may be radially deflected inwards. The stomal stop 1 may, for instance, be used for an artificial, whether or not temporary, opening.

Figure 2:
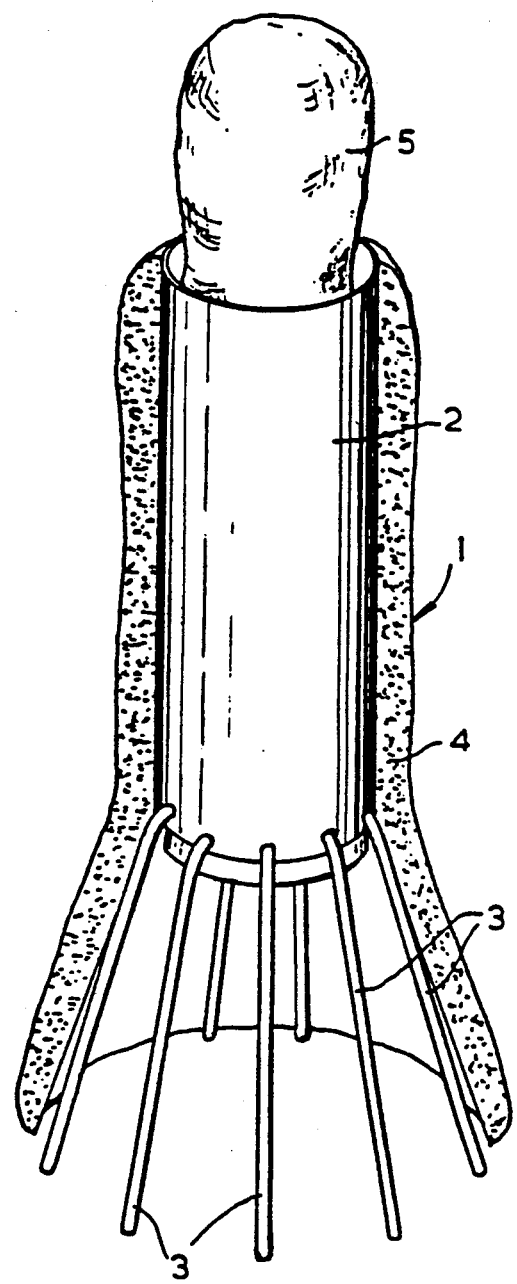

FIG. 2 depicts a stomal stop similar to that of FIG. 1. Like parts are indicated by like reference numerals. Here the reeds 3 are radially deflected outwards. This is the position which the reeds occupy, whether or not automatically, when once the stomal stop 1 has been inserted into, for example, an anus.

FIG. 3 represents a stomal stop 1 in which the support 2 has the shape of a ring. It again comprises reeds 3, fluid-absorbing material 4 and a bag 5. In the stomal stops 1 of FIG. 1-4 the support 2 may, if required, include an air filter. Such an air filter may take the form of capillary ducts.

FIG. 4 shows a cylindrical support 2 on whose outer wall a hollow helical spring 9 has been disposed. The support 2 thus provided with a helical spring 9 is enveloped in a cottonwool-like material 10 which may expand under the action of heat, for instance. The whole is surrounded by a cylindrical sleeve 11 which subjects the whole to a certain pre-compression. As soon as the stomal stop has been inserted into a skin cavity of a stomal stop user, the sleeve 11 is removed. As a result, the helical spring 9 will become slack—and thereby increase in diameter—which leads to a firm positioning of the stomal stop in the skin cavity. Under the influence of body heat of the stomal stop user, the cottonwool-like material 10 expands whereby the appliance is secured in position even better. Body gases of the stomal stop user can escape to atmosphere through the cavity of the helical spring 9. It will be obvious that the cottonwool-like material 10 and the helical spring 9 may be used either together or separately.

FIG. 5 depicts a strip of adhesive material 6 which has been stuck onto the skin 7 of stomal stop user. The strip 6 has an opening 8 through which a stomal stop according to any one of FIGS. 1-4 is to be inserted. A body-friendly skin spray may be applied in conjunction with the strip of adhesive material. Such a skin spray, which may contain urea derivatives, for example, is to be applied to the inner wall of a skin cavity of the stomal stop user so as to ensure that the inner wall is permeable to air but not to a fluids.

It is to be noted that the bag 5 is normally accommodated within the support 2 before use of the stomal stops represented in FIGS. 1-4. When the stomal stops are in use, the bag 5 will gradually be filled and in consequence thereof emerge partly from the support with its closed end. If required, a locking ring is provided to prevent the bag 5 from emerging prematurely.

I claim:

1. A stomal channel comprising:
   a support, said support being substantially circular in cross-section and having oppositely situated open ends, one end of said support configured to be received within a stoma;
   a bag at least partially surrounded by said support such that material entering said stomal channel from said stoma is substantially deposited within said bag;
   wherein said support further comprises a means for attaching said support to said stoma, said attachment means comprising a material which expands through the action of at least one of heat, fluid, and pressure, said attachment means being disposed at least partly around said support; and
   a spongy material substantially surrounding at least a portion of said support, said spongy material comprising a fluid-absorbing material which expands upon absorption of fluid to seal said stoma.

2. The stomal channel as recited in claim 1 wherein said spongy material is comprised of an open cell material such that gas may pass therethrough.

3. The stomal channel recited in claim 1 wherein said means for attachment comprises a plurality of resilient reads disposed at one end of said support, said reeds being spring biased outwardly to attach said support body to said stoma.

4. The stomal channel as recited in claim 1 wherein said means for attachment comprises a helical spring disposed within said support body, said helical spring being initially tensioned to permit passage of said support body into said stoma and thereafter being resiliently expandable to frictionally hold said stomal channel within said stoma.

5. The stomal channel as recited in claim 4 further comprising an insertion sleeve initially disposed about at least a portion of said stomal channel to tension said helical spring and being slidably removable therefrom such that, after said stomal channel has been inserted through a stoma, said sleeve may be extracted therefrom to effect expansion of said helical spring.

6. A stomal channel comprising:
   a support body having a proximal end, a distal end, and an open axial bore extending therethrough;
   a collection bag disposed at least partially within the axial bore of said support body and affixed thereto such that material passing into the support body, through the proximal end thereof, will become deposited in said bag;
   an insertion sleeve initially disposed about at least a portion of said stomal channel and being slidably removable therefrom such that, after said stomal channel has been inserted through a stoma, said sleeve may be extracted therefrom, leaving said stomal channel in an inserted position within said stoma;
   a helical spring disposed within said support body, said helical spring being initially tensioned by said insertion sleeve to permit passage of said support body into said stoma and being resiliently expandable upon removal of said insertion sleeve to frictionally hold said stomal channel within said stoma.

7. The stomal channel of claim 6 wherein said bag is initially folded so as to subsequently unfold and expand as material becomes collected in said bag.

8. The stomal channel of claim 7 wherein said helical spring is hollow to permit passage of gas therethrough.

9. The stomal channel of claim 8 further comprising a layer of sponge-like material formed about at least a portion of said support body.

10. The stomal channel of claim 9 wherein said sponge-like material comprises a plurality of open cells through which gas may pass.

11. The stomal channel of claim 8 wherein said sponge-like material contains a sufficient number of closed cells so as to readily absorb fluid.

12. The stomal channel of claim 11 wherein said support body is cylindrical in shape.

13. The stomal channel of claim 11 wherein said support body is conical in shape, said support body having a distal end which is larger in diameter than the proximal end thereof.

14. The stomal channel of claim 13 further comprising a locking ring formed about the open end of said bag, said locking ring being larger in diameter than the distal end of said conical support member, thereby serving to lock the open end of said bag, said locking ring being larger in diameter than the distal end of said conical support member, thereby serving to lock the open end of said bag within said conical support member.

* * * * *